(12) United States Patent
Hill et al.

(10) Patent No.: US 12,121,341 B2
(45) Date of Patent: Oct. 22, 2024

(54) SYSTEMS AND METHODS FOR TRACKING AND IMAGING A TREATMENT PROBE HAVING AN INTEGRATED SENSOR

(71) Applicant: Covidien LP, Mansfield, MA (US)

(72) Inventors: Morgan L. Hill, Boulder, CO (US); Jeetendra S. Bharadwaj, Erie, CO (US); Flor De Maria R. Nonalaya, Longmont, CO (US); Eric W. Larson, Littleton, CO (US); Kathy E. Rooks, Longmont, CO (US); Richard A. Willyard, Loveland, CO (US); Robert J. Behnke, II, Erie, CO (US); Nikhil P. Mankar, Pune (IN); Darren G. Girotto, Louisville, CO (US)

(73) Assignee: Covidien LP, Mansfield, MA (US)

( * ) Notice: Subject to any disclaimer, the term of this patent is extended or adjusted under 35 U.S.C. 154(b) by 221 days.

(21) Appl. No.: 17/124,687

(22) Filed: Dec. 17, 2020

(65) Prior Publication Data

US 2021/0100477 A1   Apr. 8, 2021

Related U.S. Application Data

(63) Continuation of application No. 15/600,304, filed on May 19, 2017, now Pat. No. 10,874,327.

(51) Int. Cl.
   *A61B 5/06*   (2006.01)
   *A61B 8/00*   (2006.01)
   (Continued)

(52) U.S. Cl.
   CPC ............ *A61B 5/066* (2013.01); *A61B 8/0841* (2013.01); *A61B 8/12* (2013.01); *A61B 8/4254* (2013.01);
   (Continued)

(58) Field of Classification Search
   CPC ...... A61B 18/1815; A61B 2018/00023; A61B 2018/00577; A61B 2018/00642;
   (Continued)

(56) References Cited

U.S. PATENT DOCUMENTS

| 3,868,565 A | 2/1975 | Kuipers |
|---|---|---|
| 3,983,474 A | 9/1976 | Kuipers |

(Continued)

FOREIGN PATENT DOCUMENTS

| CN | 106344150 A | 1/2017 |
|---|---|---|
| EP | 0922966 A2 | 6/1999 |

(Continued)

OTHER PUBLICATIONS

European Examination Report issued in corresponding application EP 18173304.9 dated May 12, 2022 (6 pages).

(Continued)

*Primary Examiner* — Michael T Rozanski
(74) *Attorney, Agent, or Firm* — Carter, DeLuca & Farrell LLP

(57) ABSTRACT

A system includes an energy source configured to generate therapeutic energy, a treatment probe, an ultrasound imaging device configured to generate ultrasound images, a second tracking sensor configured to track a location of the ultrasound imaging device, and a tracking system configured to receive location information from the first and second tracking sensors and to overlay the ultrasound images with a graphical representation of the treatment probe on a display based on the location information. The treatment probe includes an antenna configured to treat tissue with the therapeutic energy and a first tracking sensor integrated in the antenna and configured to track a location of a distal tip of the antenna.

15 Claims, 13 Drawing Sheets

(51) Int. Cl.
  *A61B 8/08* (2006.01)
  *A61B 8/12* (2006.01)
  *A61B 18/18* (2006.01)
  *A61B 18/00* (2006.01)
  *A61B 34/20* (2016.01)
  *A61B 90/00* (2016.01)
  *A61B 90/98* (2016.01)

(52) U.S. Cl.
  CPC .......... *A61B 8/4272* (2013.01); *A61B 8/4444* (2013.01); *A61B 8/52* (2013.01); *A61B 18/1815* (2013.01); *A61B 2018/00023* (2013.01); *A61B 2018/00577* (2013.01); *A61B 2018/00642* (2013.01); *A61B 2018/00678* (2013.01); *A61B 2018/00708* (2013.01); *A61B 2018/00791* (2013.01); *A61B 2018/00875* (2013.01); *A61B 2018/00982* (2013.01); *A61B 2018/00988* (2013.01); *A61B 2018/1892* (2013.01); *A61B 2034/2051* (2016.02); *A61B 2090/3782* (2016.02); *A61B 90/98* (2016.02)

(58) Field of Classification Search
  CPC .......... A61B 2018/00678; A61B 2018/00708; A61B 2018/00791; A61B 2018/00875; A61B 2018/00982; A61B 2018/00988; A61B 2018/1892; A61B 2034/2051; A61B 2090/3782; A61B 5/066; A61B 8/0841; A61B 8/12; A61B 8/4254; A61B 8/4272; A61B 8/4444; A61B 8/52; A61B 90/98
  See application file for complete search history.

(56) References Cited

U.S. PATENT DOCUMENTS

| | | | |
|---|---|---|---|
| 4,017,858 | A | 4/1977 | Kuipers |
| 4,054,881 | A | 10/1977 | Raab |
| 4,287,809 | A | 9/1981 | Egli et al. |
| 4,314,251 | A | 2/1982 | Raab |
| 4,328,548 | A | 5/1982 | Crow et al. |
| 4,346,384 | A | 8/1982 | Raab |
| 4,394,831 | A | 7/1983 | Egli et al. |
| 4,396,885 | A | 8/1983 | Constant |
| 4,613,866 | A | 9/1986 | Blood |
| 4,710,708 | A | 12/1987 | Rorden et al. |
| 4,737,794 | A | 4/1988 | Jones |
| 4,742,356 | A | 5/1988 | Kuipers |
| 4,849,692 | A | 7/1989 | Blood |
| 5,307,072 | A | 4/1994 | Jones, Jr. |
| 5,377,678 | A | 1/1995 | Dumoulin et al. |
| 5,600,330 | A | 2/1997 | Blood |
| 5,646,525 | A | 7/1997 | Gilboa |
| 5,729,129 | A | 3/1998 | Acker |
| 5,752,513 | A | 5/1998 | Acker et al. |
| 6,615,155 | B2 | 9/2003 | Gilboa |
| 10,874,327 | B2 | 12/2020 | Hill et al. |
| 2004/0254458 | A1 | 12/2004 | Govari |
| 2008/0294162 | A1 | 11/2008 | Rossetto et al. |
| 2012/0053577 | A1 | 3/2012 | Lee et al. |
| 2012/0143055 | A1 | 6/2012 | Ng et al. |
| 2014/0121502 | A1 | 5/2014 | Vignon et al. |
| 2014/0259641 | A1* | 9/2014 | Brannan .......... A61B 18/1815 29/602.1 |
| 2016/0030111 | A1* | 2/2016 | Ladtkow .......... A61B 18/1815 606/33 |
| 2016/0051327 | A1 | 2/2016 | Brannan |
| 2016/0128669 | A1 | 5/2016 | Hill et al. |
| 2017/0135760 | A1 | 5/2017 | Girotto et al. |

FOREIGN PATENT DOCUMENTS

| | | |
|---|---|---|
| WO | 9404938 A1 | 3/1994 |
| WO | 9605768 A1 | 2/1996 |
| WO | 99/32033 A1 | 7/1999 |
| WO | 2011066445 A2 | 6/2011 |
| WO | 2013090558 A1 | 6/2013 |
| WO | 2016176549 A1 | 11/2016 |

OTHER PUBLICATIONS

Examination Report issued by the Australian Intellectual Property Office dated May 10, 2019 in corresponding Australian Patent Application No. 2018203457.

Office Action issued by the Canadian Intellectual Property Office dated Jun. 14, 2019 in corresponding Canadian Patent Application No. 3,004,670.

Sindram et al., "Novel 3-D Laparoscopic Magnetic Ultrasound Image Guidance for Lesion Targeting," HPB, Dec. 1, 2010, pp. 709-716, vol. 12, No. 10.

Partial European Search Report issued by the European Patent Office in corresponding European Patent Application No. 18173304 and dated Oct. 25, 2018 (completed on Oct. 16, 2018).

International Search Report for International Application No. PCT/US2015/05911, dated Jan. 26, 2016, 2 pages.

Extended European Search Report issued by the European Patent Office dated Jan. 28, 2019 in corresponding European Patent Application No. 18173304.9.

Australian Examination Report issued in corresponding Appl. No. AU 2018203457 dated Feb. 19, 2020 (3 pages).

Australian Examination Report No. 3 issued in corresponding Appl. No. AU 2018203457 dated Apr. 21, 2020 (3 pages).

* cited by examiner

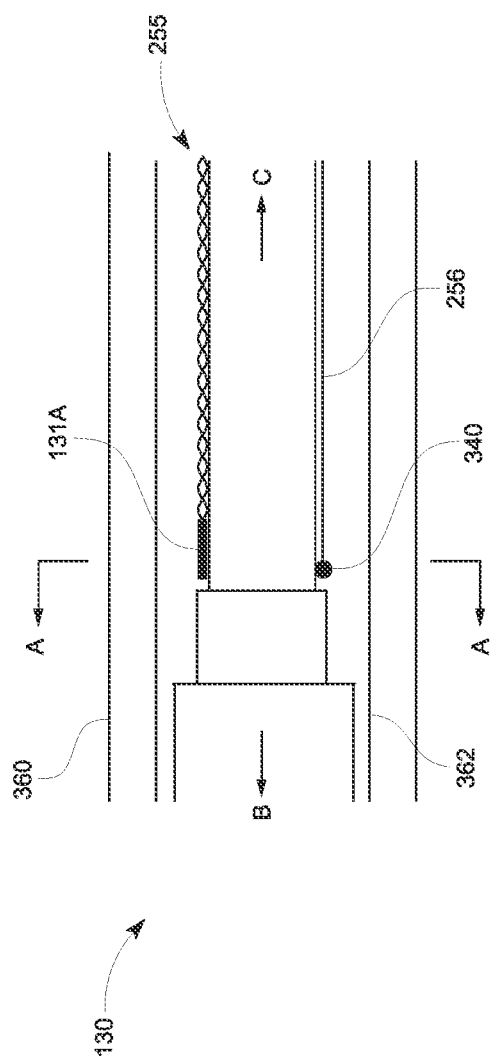
FIG.3B
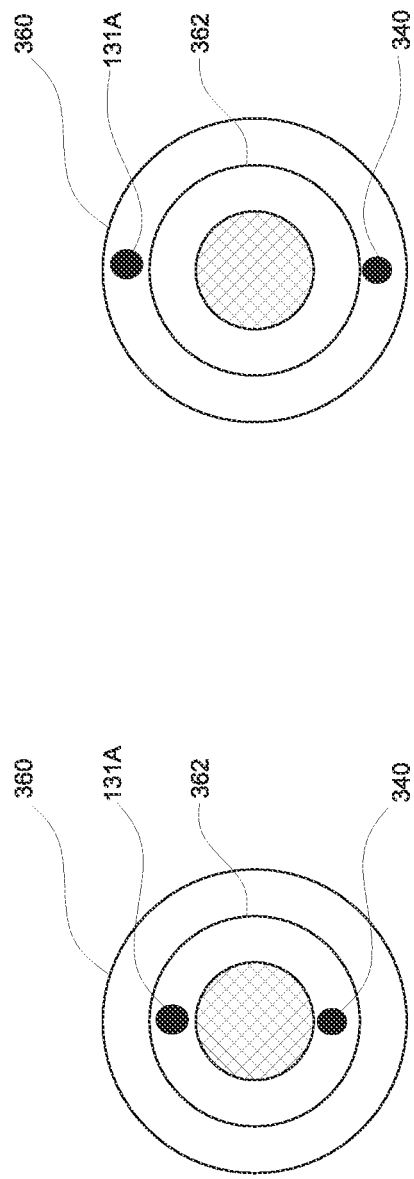
FIG.3C
FIG.3D

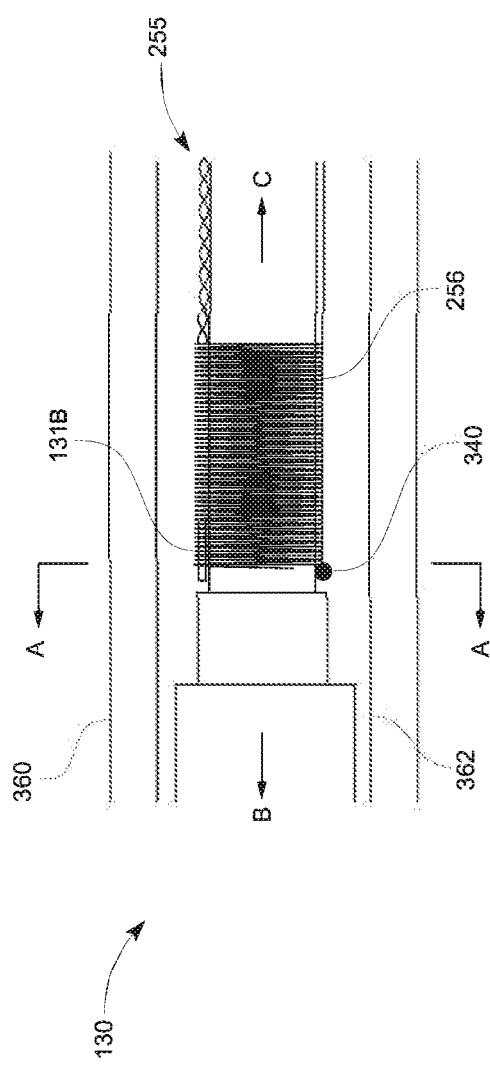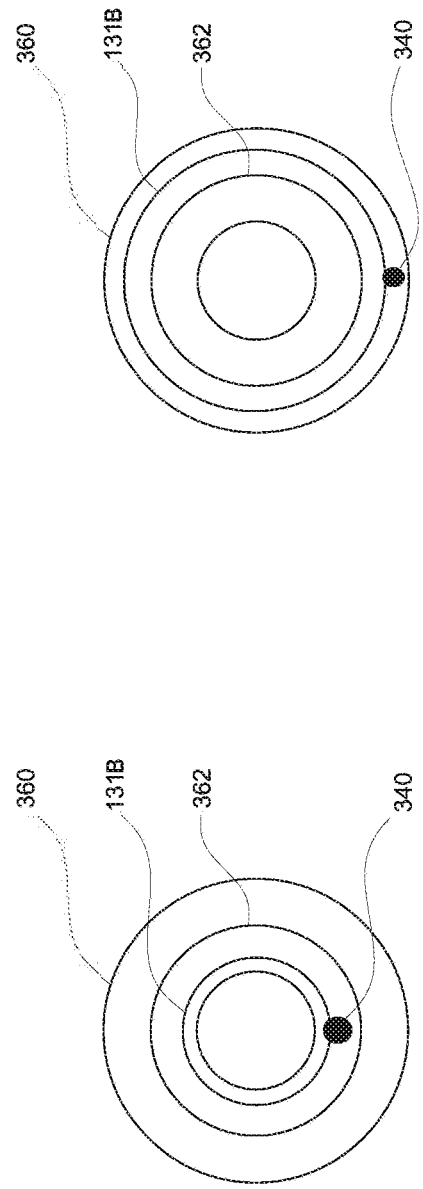

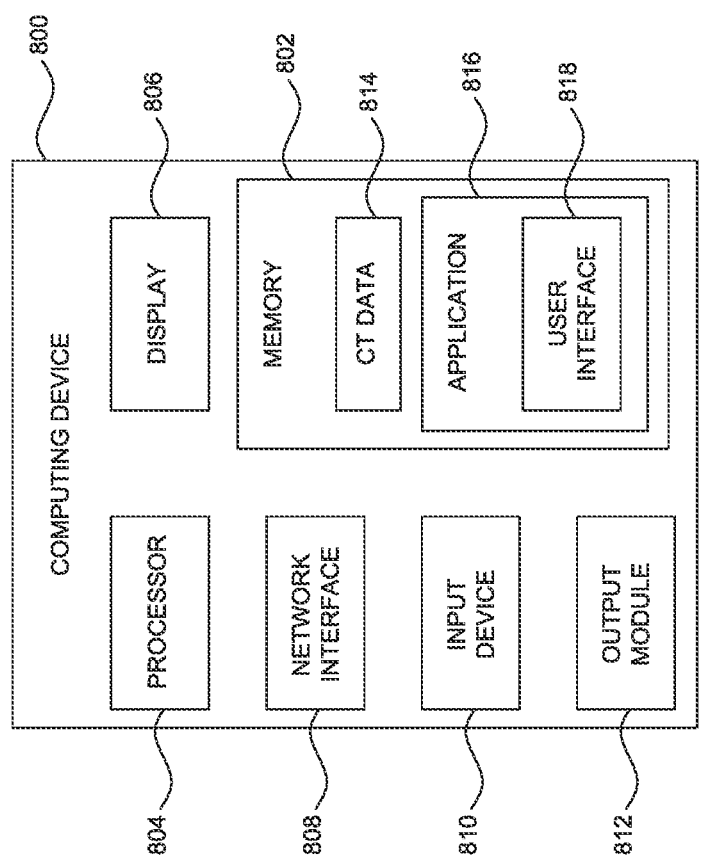

SYSTEMS AND METHODS FOR TRACKING AND IMAGING A TREATMENT PROBE HAVING AN INTEGRATED SENSOR

CROSS-REFERENCE TO RELATED APPLICATIONS

This application is a continuation of U.S. patent application Ser. No. 15/600,304, filed on May 19, 2017.

INTRODUCTION

The present disclosure relates to systems for tracking and imaging a treatment probe. More particularly, the present disclosure relates to systems for tracking and imaging a treatment probe using a tracking sensor integrated in the treatment probe.

BACKGROUND

When treating patients, clinicians often rely on patient data including X-ray data, computed tomography (CT) scan data, magnetic resonance imaging (MRI) data, or other imaging data that allows the clinician to view the internal anatomy of a patient. The patient data is typically stored off-line and is used by the clinician to identify targets of interest and to develop strategies for accessing the targets of interest for a surgical procedure. Once identified, the clinician may utilize a treatment probe to perform at least a portion of the surgical procedure.

Although useful, this off-line information may not enable a clinician to effectively track the real-time location of the treatment probe disposed inside a patient's body during the surgical procedure. Generally, in order to track the location of the treatment probe, a tracking sensor is attached to the treatment probe. However, if the tracking sensor is not firmly attached to the treatment probe, the tracking sensor moves with respect to the treatment probe as the treatment probe navigates toward and treats the targets of interest in the patient, and, as a result, the location of the treatment probe sensed by the tracking sensor does not have sufficient accuracy. Thus, there is a need that the tracking sensor is fixedly attached to or in the treatment probe. Further, it is necessary that capability of the tracking sensor is not interfered with the therapeutic energy used by the treatment probe and that capability of the therapeutic energy is not interfered with the tracking sensor.

SUMMARY

Systems for tracking and imaging a treatment probe including an integrated sensor thereon for laparoscopic operations are provided herein below.

According to an embodiment of the present disclosure, a system includes an energy source configured to generate therapeutic energy, a treatment probe, an ultrasound imaging device configured to generate ultrasound images, a second tracking sensor configured to track a location of the ultrasound imaging device, and a tracking system configured to receive location information from the first and second tracking sensors and to overlay the ultrasound images with a graphical representation of the treatment probe on a display based on the location information. The treatment probe includes an antenna configured to treat tissue with the therapeutic energy and a first tracking sensor integrated in the antenna and configured to track a location of a distal tip of the antenna.

In an aspect, the first tracking sensor is integrated on the antenna. The treatment probe further includes an inflow tube configured to wrap around a portion of the antenna and to cool down the antenna. The first tracking sensor is integrated into the inflow tube or integrated on an outer surface of the inflow tube.

In another aspect, the treatment probe includes a balun located near a distal end of the antenna, and the first tracking sensor is located at a proximal end of the balun.

In yet another aspect, the treatment probe further includes a cooling jacket surrounding the inflow tube and extending to the proximal end of the antenna and the first tracking sensor is located inside of the cooling jacket.

In still another aspect, the system further includes a disposable cable configured to provide therapeutic energy to the antenna and a reusable cable configured to connect the disposable cable to the energy source. The system further includes a first connector configured to connect the disposable cable to the reusable cable and a second connector configured to connect the reusable cable to the energy source. The treatment probe includes a sensor wire connected to the first tracking sensor and configured to transmit sensed results from the first tracking sensor to the tracking system, where the sensor wire extends inside of the disposable cable and branches out from the disposable cable prior to the first connector. In an aspect, the sensor wire extends inside the disposable cable, the first connector, and the reusable cable, and branches out from the reusable cable prior to the second connector, or the sensor wire extends inside the disposable cable, the first connector, the reusable cable, and the second connector.

In yet still another aspect, the system further includes a display configured to display the location of the treatment probe with respect to at least one target in the overlaid ultrasound images with the graphical representation, based on a spatial relationship between the location of the treatment probe and the location of the ultrasound imaging device.

According to another embodiment of the present disclosure, the system includes an energy source configured to generate therapeutic energy, a treatment probe, a first tracking sensor configured to track a location of a distal tip of the antenna, an ultrasound imaging device configured to generate ultrasound images, a second tracking sensor configured to track a location of the ultrasound imaging device, and a tracking system configured to receive location information from the first and second tracking sensors and to overlay the ultrasound images with a graphical representation of the treatment probe on a display based on the location information. The treatment probe includes an antenna configured to treat tissue with the therapeutic energy, and a hub configured to prevent the antenna from moving with respect to the hub.

In an aspect, the first tracking sensor is affixed to an outer surface of the hub. The hub includes a recess configured to receive the first tracking sensor.

In another aspect, the system further includes a display configured to display the location of the treatment probe with respect to at least one target in the overlaid ultrasound images with the graphical representation, based on a spatial relationship between the location of the treatment probe and the location of the ultrasound imaging device.

In yet another aspect, the system further includes a pair of retrofits covering a portion of the hub, when the pair of retrofits is mated. The system further includes a sensor wire connected to the first tracking sensor and configured to transmit sensed results from the first tracking sensor to the tracking system. The system according where at least one of the pair of the retrofits includes a recess configured to receive the sensor wire. The system further includes a cable configured to provide therapeutic energy to the antenna from the energy source and the cable runs separately from the sensor wire.

Any of the above aspects and embodiments of the present disclosure may be combined without departing from the scope of the present disclosure.

BRIEF DESCRIPTION OF THE DRAWINGS

Objects and features of the presently disclosed system and method will become apparent to those of ordinary skill in the art when descriptions of various embodiments thereof are read with reference to the accompanying drawings, of which:

FIGS. 3B-3D are schematic diagrams of a portion of the treatment probe, illustrating a cylinder type tracking sensor in accordance with embodiments of the present disclosure;

FIGS. 3E-3G are schematic diagrams of a portion of the treatment probe, illustrating a hollow type tracking sensor in accordance with embodiments of the present disclosure;

FIG. 8 is a schematic diagram of a computing device which forms a part of the tracking and treatment system 10 of FIG. 1 in accordance with an embodiment of the present disclosure.

DETAILED DESCRIPTION

The present disclosure is directed to systems and methods with integrated tracking sensors into treatment probes for tracking and imaging a treatment probe used in laparoscopic surgical procedures. While performing the surgical procedure, it is important to determine an exact location of the treatment probe within a patient's body, and an angle and a direction at which the treatment probe is approaching a target of interest. In addition, it is beneficial to see an image of the treatment probe as it is traversing tissue or entering the target of interest. Moreover, it is important to know where the treatment probe is located with respect to an imaging device.

In this regard, the present disclosure describes features related to a tracking sensor, with which a spatial relationship between the treatment probe and an imaging device can be determined as the treatment probe is navigated to a target of interest within the patient in combination with real-time images of the treatment probe and the target as well as surrounding tissues.

The tracking sensors are firmly mounted or integrated on or in the treatment probe to track real-time locations of the treatment probe and to ensure accuracy of the location of the distal tip (e.g., an antenna or a pair of jaw members) of the treatment probe. The location of the distal tip of the treatment probe is identified by a predetermined distance between the tracking sensor and the distal tip of the treatment probe.

Further, the present disclosure describes various cable management configurations to be implemented between the tracking sensor and the treatment and tracking system.

In an embodiment, medical treatments, according to the present disclosure, are generally divided into two phases: (1) a planning phase, and (2) a procedure phase. The planning phase of medical treatment (e.g., microwave ablation) is more fully described in patent application Ser. No. 14/821,912 entitled "TREATMENT PROCEDURE PLANNING SYSTEM AND METHOD" filed on Aug. 10, 2015, by Bharadwaj et al., the contents of which is hereby incorporated by reference in its entirety.

Although the present disclosure will be described in terms of specific illustrative embodiments, it will be readily apparent to those skilled in this art that various modifications, rearrangements and substitutions may be made without departing from the spirit of the present disclosure. The scope of the present disclosure is defined by the claims appended hereto.

Figure 1:
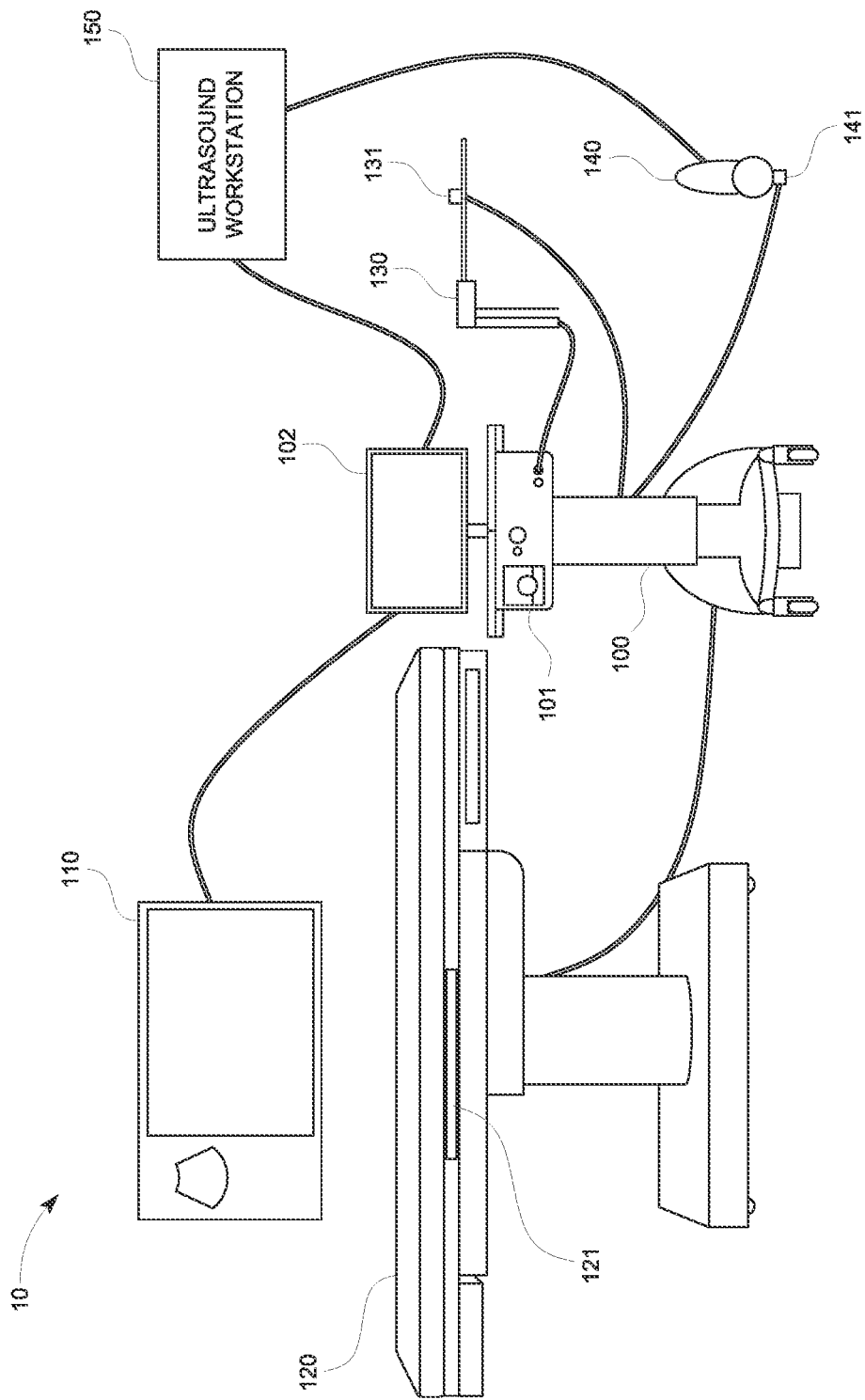
FIG. 1 is a schematic diagram of a tracking and treatment system in accordance with an illustrative embodiment of the present disclosure.

Referring now to FIG. 1, the present disclosure is generally directed to enabling tools or treatment probes 130 to be useable with a tracking and treatment system 10, which includes a tracking system 100, an electrosurgical generator 101, a workstation 102, a display 110, a table 120, the treatment probe 130, an imaging device 140, and an ultrasound workstation 150. The tracking system 100 may be, for example, a laptop computer, desktop computer, tablet computer, or other similar device. The workstation 102 may also be used to control a cooling pump or other peripheral devices not expressly shown in FIG. 1. The tracking system 100 may interact with an EM field generator 121, one or more tracking sensors 131 and 141 (e.g., an EM sensor, though others could be used), and the display 110 on which a user interface presents the location of the tracking sensors 131 in the EM field in combination with one or more imaging modalities. The tracking system 100 includes software which converts signals received from the tracking sensors 131 and 141 and performs necessary calculations to track the location of the EM sensors in an EM field generated by the EM field generator 121. In addition to tracking information, the display 110 presents to a user the results of the software processing including instructions, images, and messages relating to the performance of the procedure.

The EM field generator 121 may be built into the table 120 and located under a patient thus generating an EM field around a portion of the patient's body through which navigation to a target is desired. Typically, this may be the patient's torso which enables navigation to and treatment of all the major organs of the body. However, the same system could be used to treat other locations on the patient. An example of the EM field generator 121 is the AURORA™ system sold by Northern Digital Inc. The location of the EM field generator 121 is not limited to under the patient but may be located above, to the side of, or around the patient. Further, the EM field generator 121 may be movable to a desired location of the patient.

The electrosurgical generator 101 generates electrosurgical energy (e.g., radio frequency wave or microwave) and provides the generated energy to the treatment probe 130. The treatment probe 130 is a surgical instrument, for example, a microwave ablation antenna used to ablate and treat tissue. Various other surgical instruments or surgical tools, such as electrosurgical pencils, vessel sealers, staplers, resection devices and others, may also be used with the tracking system 100 either with or without the tracking sensor 131. In one embodiment, the tracking sensor 131 is located on the treatment probe 130, as will be described in detail below, allowing for the tracking of the location of the treatment probe 130 in the EM field. While the present disclosure describes the use of the tracking and treatment system 10 in a surgical environment, it is also envisioned that some or all of the components of the tracking and treatment system 10 may be used in alternative settings, for example, at a treatment review board or other office setting such as during a post treatment review of the procedure or assessment of progress of the patient.

Along with the tracking system 100, the tracking and treatment system 10 includes capabilities for obtaining images of the patient, target, and the treatment probe 130 using ultrasound imaging. The imaging device 140, which may be an ultrasound wand, is used to image the patient's body during the procedure to thereby provide visualization of the location of surgical instruments, such as the treatment probe 130, inside the patient's body. The imaging device 140 may be positioned in relation to the treatment probe 130 such that the treatment probe 130 is imaged during navigation to the target at an angle, thereby enabling the clinician to visualize the spatial relationship between the treatment probe 130 and the target.

Further, the tracking system 100 may also track the location of imaging device 140 using a tracking sensor 141 mounted thereto. The tracking sensors 141 and 131 may be EM sensors. The tracking sensors 131 and 141 may be a six (6) degrees-of-freedom (DOF) sensor. Alternatively, to achieve 6 DOF a combination of two AURORA® 5 DOF sensors sold by Northern Digital Inc., which can resolve 6 DOF may be employed. Alternatively, the tracking sensor 131 or 141 includes only one sensor resolving the required DOF.

In an embodiment in which the tracking sensor 131 is a 5 DOF sensor, three translational movements are sensed in X, Y, and Z directions and two rotations are sensed in pitch and yaw directions. When the tracking sensor 131 senses strengths or variations of the EM field in 5 directions, the tracking system 100 is capable of calculating the current location, translational direction, and rotational direction of the tracking sensor 131 such that an angle and a direction of the treatment probe 130 approaching a target can be identified. Also, based on these rotational and translational movements of the imaging device 140, the ultrasound image plane moves and/or rotates on the display 110, correspondingly. This 5 DOF sensor may be used when the treatment probe 130 is longitudinally straight and/or roll rotations does not affect any changes to the location of the distal tip of the treatment probe 130.

In an aspect, the tracking sensor 131, which can resolve 6 DOF, may be used with the treatment probe 130 and sense three translational movements and three rotational movements, i.e., pitch, yaw, and roll. This 6 DOF sensor may be used when the treatment probe 130 is not longitudinally straight and/or any roll rotations result in changes to the location of the distal tip of the treatment probe 130.

The workstation 102 is configured to combine the ultrasound images from the ultrasound workstation 150 and EM data from the tracking system 100. The EM data may include the location of the distal tip of the treatment probe 130 and the movement direction of the treatment probe 130. The workstation 102 generates images using the EM data to depict the treatment probe 130, pre-stored images of the treatment probe 130, and the live ultrasound images, and displays the generated images on the display 110 based on the location and movement direction of the treatment probe 130. In an aspect, the workstation 102 may be configured to calculate the spatial relationship between the treatment probe 130 and the imaging device 140 from the EM data and the ultrasound data to thereby generate a representation of the location of the treatment probe 130 in the ultrasound images. As a result, the treatment probe 130 is depicted with respect to the imaging plane of the imaging device 140. Additionally, either a pre-planned or a live-planned pathway to a target may also be overlaid in the ultrasound image allowing the clinician to visualize the pathway to reach the target.

Figure 2:
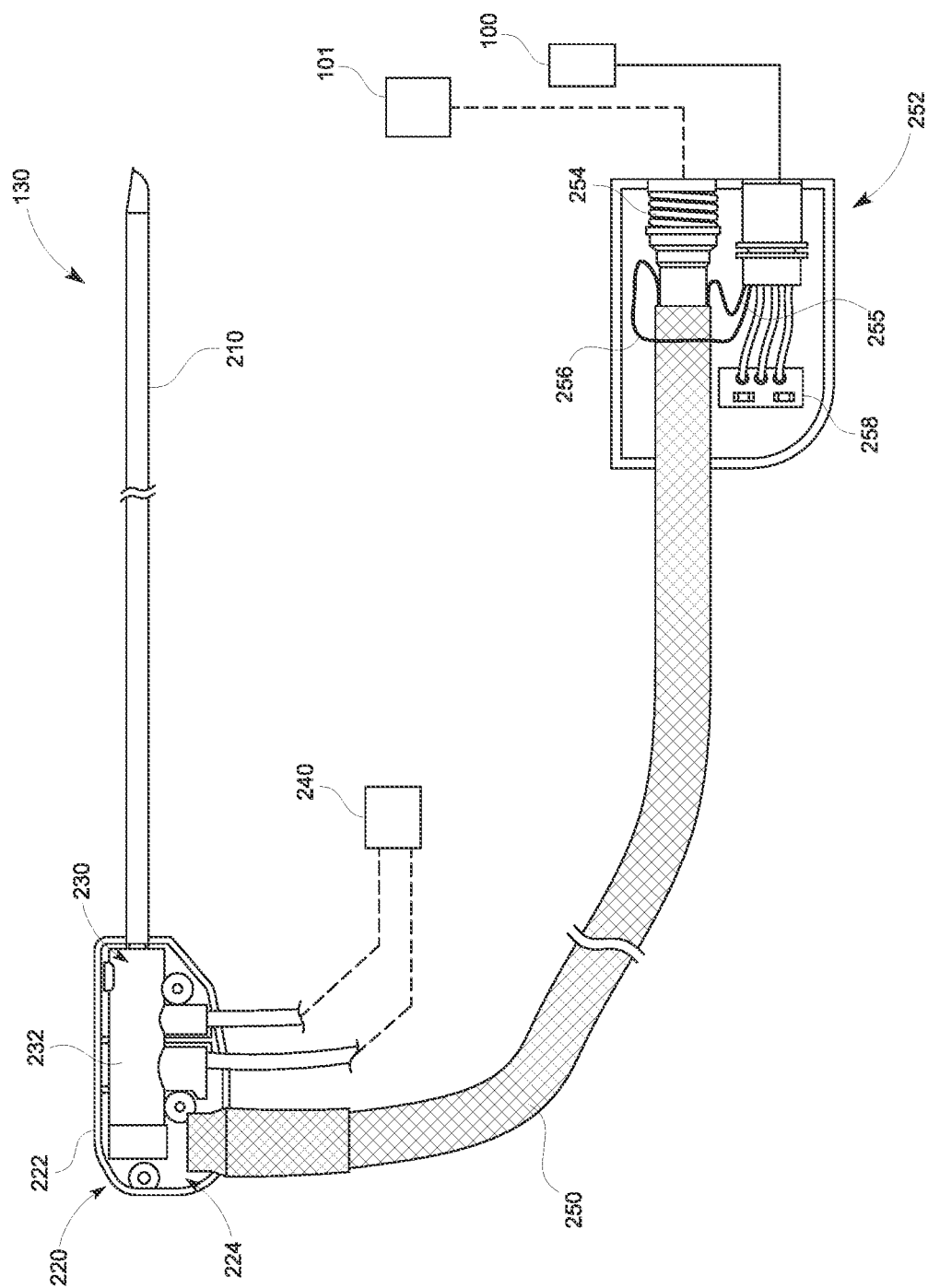
FIG. 2 is a schematic diagram of a treatment probe including an antenna, a hub assembly, and a connector assembly in accordance with an embodiment of the present disclosure.

Referring now to FIG. 2, the treatment probe 130 of the tracking and treatment system 10 is shown in accordance with an embodiment. The treatment probe 130 includes an antenna 210 extending from a handle assembly 220 and coupled to the electrosurgical generator 101 and the tracking system 100 via a cable 250. The handle assembly 220 includes a handle body 222 defining a handle-body chamber 224 within which a hub 230 is disposed. The hub 230 is made up of a hub body 232 defining a hub-body chamber therein. In some aspects, the hub body 232 may include one or more mechanical interfaces adapted to matingly engage with one or more corresponding mechanical interfaces associated with the handle body 222 to align the hub 230 within the handle body 222 and/or to fixedly secure the hub 230 within the handle-body chamber 224. Although not depicted in FIG. 2, as shown in FIGS. 3A-3G and 5, the tracking sensor may be attached to or incorporated in or on either the antenna 210 or the hub body 232. To reduce the temperature of the antenna 210 during electrosurgical operations, the hub 230 includes an inlet/outlet coupled to a coolant supply system 240, which provides a coolant to the antenna 210.

The cable 250 may include a connector assembly 252, which is an interface between the cable 250 and the tracking system 100 and the electrosurgical generator 101. The connector assembly 252 may house a connector 254 for a transmission line (e.g., a coaxial cable) to the treatment probe 130, another connector for a temperature sensor wire 256, the tracking sensor wire 255, and a circuit 258. The temperature sensor wire 256 may be disposed within the cable 250 together with the tracking sensor wire 255, or the tracking sensor wire 255 may be separate from the cable 250. In an aspect, the circuit 258 may include a memory for storing the spatial relationship between the tracking sensor 131 and the distal tip of the treatment probe 130 and other data such as usage or in-use data (e.g., historical indicators of the manner in which the device was used).

Figure 3A:
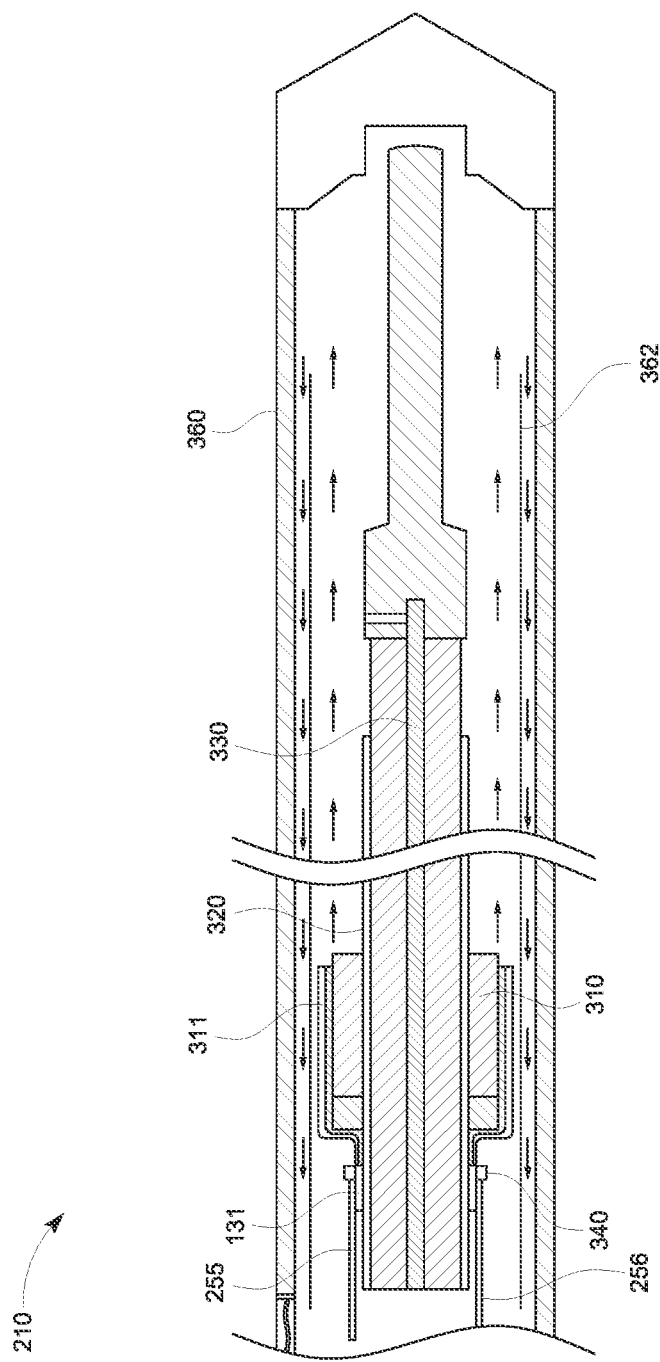
FIG. 3A is a broken, longitudinal cross-sectional, partial view of the distal portion of a treatment probe, illustrating the tracking sensor 131 of FIG. 1 incorporated in the antenna 210 of FIG. 2 in accordance with an embodiment of the present disclosure.

According to embodiments, the tracking sensor 131 is integrated with and tracks the treatment probe 130, and may be disposed at any one of various locations. FIG. 3A is a longitudinal cross-sectional view of the antenna 210 including the tracking sensor 131 integrated therewith, according to an embodiment of the present disclosure. The antenna 210 may include a balun 310 disposed proximal to but spaced apart from the distal end of the antenna 210. An outer conductor 320 of the cable 250, which is a part of the transmission line for the antenna 210, extends beyond the distal end of the balun 310 and forms part of the radiating section of antenna 210. A portion of the balun 310 is surrounded by an outer heat shrink tubing 311, which includes an electrically conductive layer disposed around the outer peripheral surface of the balun 310. In an aspect, due to the temperature raised by radiation of energy by the antenna 210, the tracking sensor 131 may be positioned near a proximal portion of the balun 310.

The antenna 210 may also include a temperature sensor 340, which is positioned proximal to the balun 310 and connected to the temperature sensor wire 256 and which transmits sensed temperatures through the cable 250. In an aspect, the tracking sensor 131 may be positioned near the temperature sensor 340. Since the temperature sensor 340 is located away from the distal tip of the antenna 210 so as not to be influenced by the heat generated by the antenna 210 but is close enough to accurately measure temperature of the tissue treated by the antenna 210, spatial proximity to the temperature sensor 340 ensures that the tracking sensor 131 functions within its tolerance range, as the temperature sensor 340 does. The spatial proximity may indicate that the tracking sensor 131 is located close to the antenna 210 but outside a predetermined distance from the antenna 210. Thus, the tracking sensor 131 is capable of compensating for influence from the energy radiated by the antenna 210 when the temperature sensor 340 is within the spatial proximity.

In an embodiment, the antenna 210 further includes a cooling jacket 360 and an inflow tube 362. The inflow tube 362 is tubular and extends along a portion of the length of the cable 250. The cooling jacket 360 extends coaxially with the inner cooling jacket and terminates proximate the distal end of the antenna 210. In an aspect, the tracking sensor 131 may be integrated on the inner surface of the inflow tube 362 or on the outer surface of the inflow tube 362. In this way, temperature surrounding the tracking sensor 131 is controlled so that the tracking sensor 131 may function within its tolerance range.

By integrating the tracking sensor 131 in the antenna 210, the spatial relationship between the tracking sensor 131 and the distal tip of the antenna 210 is predetermined and can be compensated for by the location sensing software. Consequently, the tracking system 100 can calculate the location of the distal tip of the antenna 210 with further accuracy.

FIGS. 3B-3D illustrate a cylinder type tracking sensor 131a according to embodiments of the present disclosure. FIG. 3B shows a schematic diagram illustrating a longitudinal cross-sectional view of the treatment probe 130 of FIG. 1 and FIGS. 3C and 3D show schematic diagrams illustrating a transverse cross-sectional view with respect to A-A direction of the treatment probe 130 of FIG. 3B. "B" represents a direction toward to the radiating section of the antenna 210 and "C" represents a direction toward the handle assembly 220. The cylinder type tracking sensor 131a is connected to the tracking system 100 via twisted wires 255 and the temperatures sensor 340 is connected to the tracking system 100 via the wire 256. Since the cylinder type tracking sensor 131a takes up very little small space, the cylinder type tracking sensor 131a may be located or positioned inside of the inflow tube 362 as shown in FIG. 3C or between the inflow tube 362 and the cooling jacket 360 as shown in FIG. 3D. In an aspect, the temperature sensor 340 may be positioned inside the inflow tube 362 as shown in FIG. 3C or between the inflow tube 362 and the cooling jacket 360 as shown in FIG. 3D, together with the tracking sensor 131a or independent from the position of the tracking sensor 131a. In another aspect, the shape of the cylinder type tracking sensor 131a is not limited to a circular solid but may be any shape suitable to fit in the small space of the antenna 210.

FIGS. 3E-3G illustrate a hollow type tracking sensor 131b according to embodiments of the present disclosure. FIG. 3E shows a schematic diagram illustrating a longitudinal cross-sectional view of the treatment probe 130 of FIG. 1, and FIGS. 3F and 3G show schematic diagrams illustrating a transverse cross-sectional view with respect to A-A direction of the treatment probe 130 of FIG. 3E. Directions regarding "B" and "C" are described above with respect to FIG. 3B. Since the hollow type tracking sensor 131b takes up very little space, the hollow type tracking sensor 131b may be located or positioned wrapped around the cable 250 inside of the inflow tube 362 as shown in FIG. 3F or on an outer surface of the inflow tube 362 as shown in FIG. 3G.

In another aspect, the cylinder type tracking sensor 131a or the hollow type tracking sensor 131b may be located or positioned around the cooling jacket 360. In this case, the twisted wires 255 and the wire 256 may run along the outer surface of the antenna 210.

The tracking sensor 131a or 131b may be positioned opposite to the location where the temperature sensor 340 is positioned as shown in FIGS. 3C, 3D, 3F, and 3G. In an aspect, the relative locations between the tracking sensors 131a, 131b and the temperature sensor 340 may be not opposite to each other. In another aspect, the tracking sensors 131a, 131b and the temperature sensor 340 may be positioned at levels different from each other. For example, the tracking sensor 131a or 131b may be positioned between the inflow tube 362 and the cooling jacket 360 and the temperature sensor 340 may be positioned within the inflow tube 362.

Figure 3H:
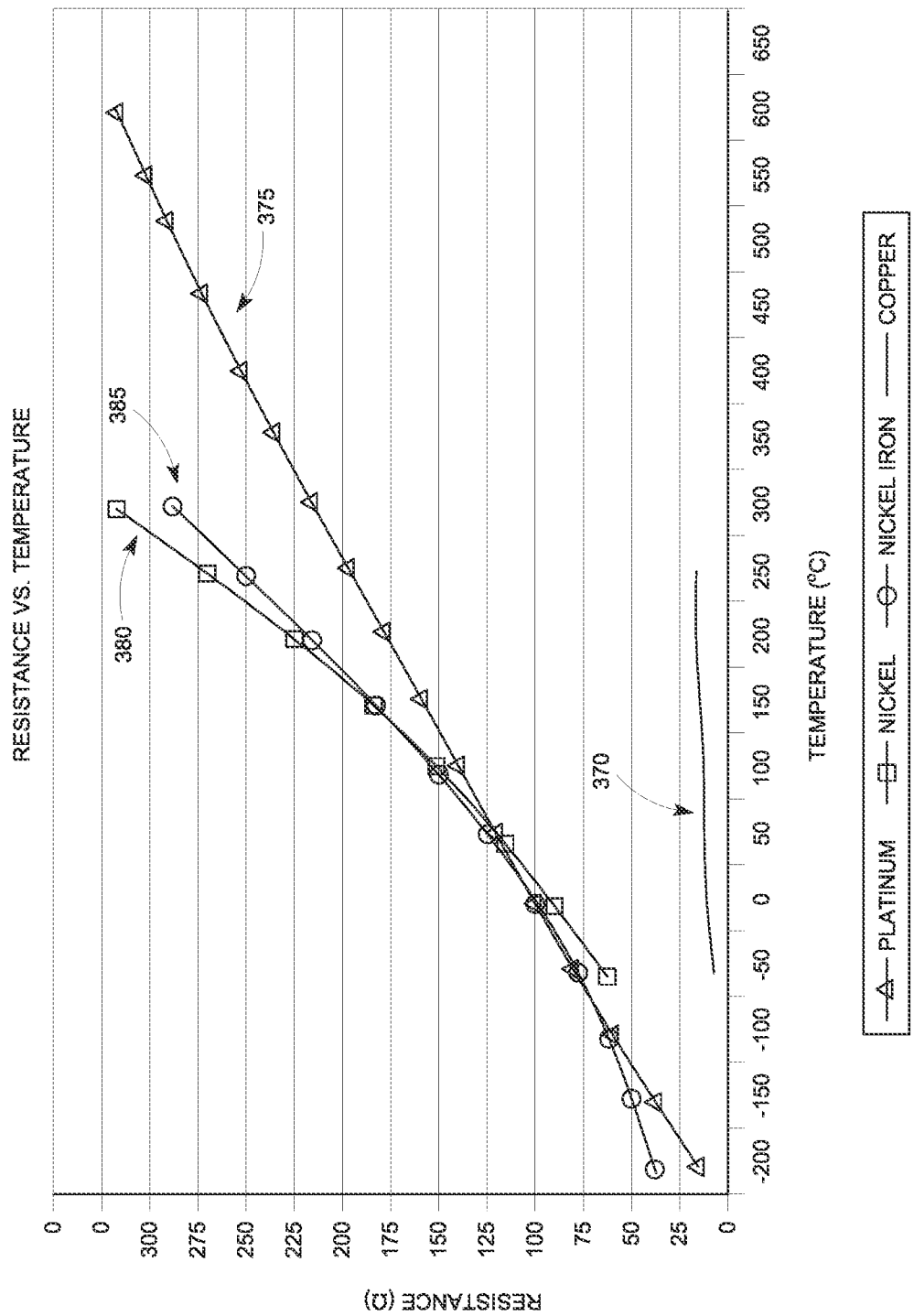
FIG. 3H is a graphical representation of relationships between the resistance of the twisted wires of the tracking sensor 131 of FIG. 1 and the temperature of the antenna 210 of FIG. 2 in accordance with embodiment of the present disclosure.

As described above, the temperature sensor 340 may be positioned near the tracking sensor 131a, 131b. An understanding of the temperatures experienced proximate to the tracking sensors 131a, 131b is important as temperature can have an impact on the resistance, and therewith current in the tracking sensor 131a or 131b. As the temperature of the antenna 210 goes up, the resistance of the twisted wires 255 of the tracking sensor 131a, 131b goes up and affects the amount of current passing through the twisted wires 255 to be sensed by the tracking system 100. Thus, the tracking system 100 may take the characteristic of the materials of the twisted wires 255 and the wires of the tracking sensor 131a, 131b into consideration when tracking the location of the antenna 210. FIG. 3H illustrates this relationship between the resistance of the twisted wires 255 and the temperature of the antenna 210 sensed by the temperature sensor 340. The horizontal axis represents temperatures of the antenna 210 and the vertical axis represents the resistance of the twisted wires 255. Further, different materials have different resistance profiles with respect to changes in temperature. In some instances the twisted wires 255 may be made up of different materials, such as copper, platinum, nickel-iron, and nickel. The materials shown in FIG. 3H are just examples and not intended to limit the range of materials for the twisted wires 255.

The curve 370 shows that copper twisted wires experiences a small increase in resistance as the temperature increases compared to the other materials. The curve 375 shows that platinum twisted wires have substantially linear relationship between temperature and resistance. The curves 380 and 385 show relationships of the nickel twisted wires and nickel-iron twisted wires, respectively. These curves 370-385 may be used to generate a thermal profile for the tracking sensor 131a, 131b based on the material of the twisted wires 255 or the tracking sensor 131a, 131b.

In embodiments, based on the thermal profile and the material of the twisted wires 255 and the tracking sensor 131a, 131b, temperature of the antenna 210 may be estimated based on the resistance of the twisted wires 255 of the tracking sensor 131a, 131b during a medical procedure using the antenna 210. Thus, the resistance of the twisted wires 255 can be used to determine whether the temperature sensor 340 is functioning correctly or the temperature is in an operable range of the antenna 210 and/or the tracking sensor 131a, 131b. In an aspect, the temperature sensor 340 may be removed from the antenna 210 and instead temperature may be determined by using the thermal profile and the material of the twisted wires 255. In another aspect, the tracking system 100 may store the thermal profile in lookup table format and use the lookup table to estimate a temperature of the antenna 210 based on the resistance of the twisted wires 255 or can trigger the electrosurgical generator 101 to discontinue therapeutic energy if the resistance reaches a temperature threshold of the treatment probe 130. Further, based on the estimated temperature, accuracy of the tracking sensor 131a, 131b may be adjusted.

In another embodiment, the amount of current passing through the twisted wires 255 may be adjusted in response to the changes in resistance of the twisted wires 255 based on the thermal profile and the temperature sensed by the temperature sensor 340. In this way, the accuracy of the tracking sensor can be improved and thus more reliable locations of the antenna 210 can be calculated.

Figure 4A:
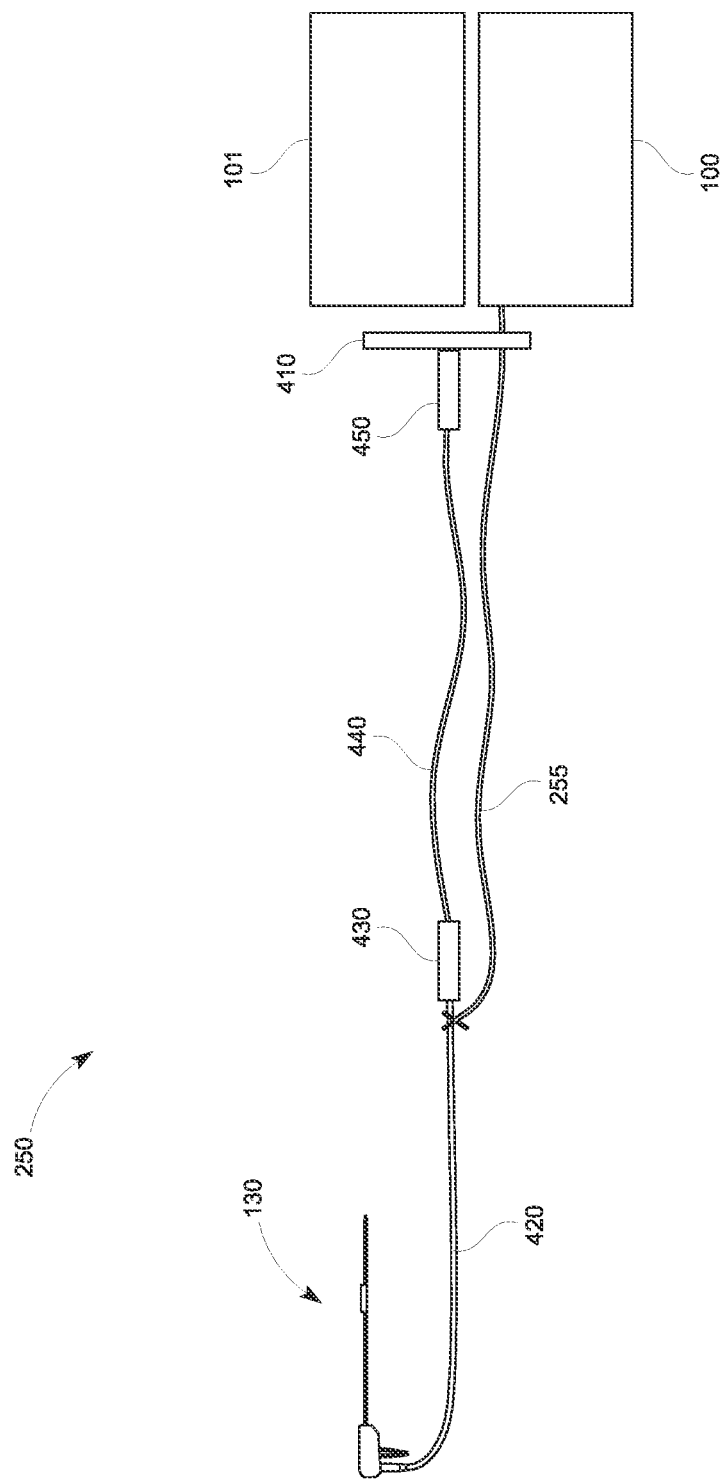
FIGS. 4A-4C are graphical representations illustrating various illustrative cable management configurations for the tracking sensor 131 in accordance with embodiments of the present disclosure.
Figure 4B:
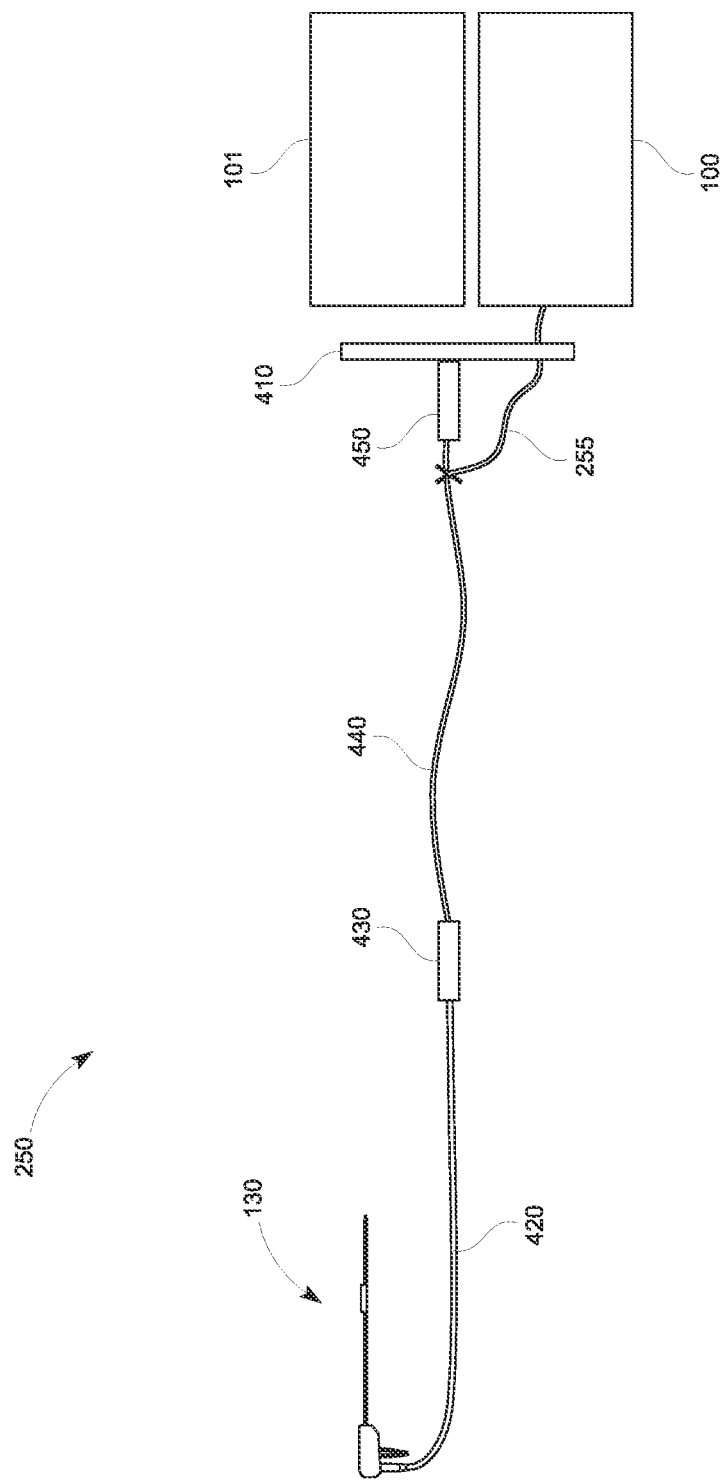
Figure 4C:
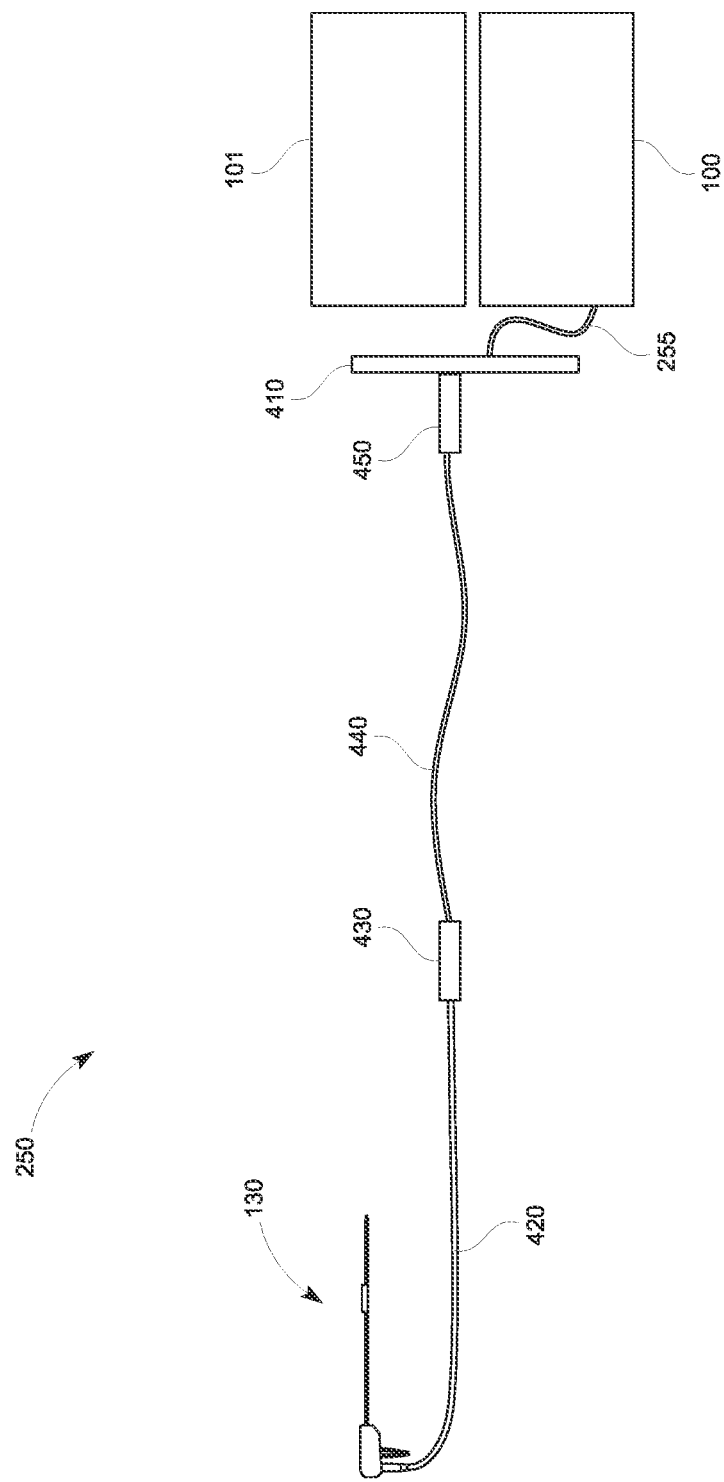

FIGS. 4A-4C are simplified diagrams of the tracking system 100 including the tracking sensor 131a or 131b integrated into the antenna 210 showing various embodiments of cable management configurations. Generally, the cable 250 includes a disposable cable 420 and a reusable cable 440 coupled to an interface 410 to thereby connect the treatment probe 130 to the electrosurgical generator 101 and the tracking system 100. The disposable cable 420 may be sufficient in length such that the reusable cable 440 does not enter into a sterilized area during the medical procedures. The disposable cable 420 separates the reusable cable 440, the electrosurgical generator 101, and the tracking system 100 from the sterilized area and is connected to the treatment probe 130 on one end and to a disposable connector 430 on the other end. The disposable connector 430 may include a memory for storing identification information of the treatment probe 130 and related information, which may include the spatial relationship between the tracking sensor 131a or 131b and the distal end of the antenna 210. In an aspect, the disposable cable 420 and the disposable connector 430 may be used only once or a predetermined number of times to keep the sterilized area from contamination. The memory of the disposable connector 430 may also include information regarding the predetermined number of times of use of the disposable cable 420. The reusable cable 440 extends from the disposable connector 430 and is connected to a reusable connector 450, which is coupled to the interface 410 to transmit any information from the treatment probe 130 to the tracking system 100 and therapeutic energy generated by the electrosurgical generator 101 to the treatment probe 130.

In an embodiment shown in FIG. 4A, the tracking sensor wire 255 may extend inside the disposable cable 420 from the handle assembly 220 and branch out from the disposable cable 420 at a location prior to the disposable connector 430. After the branch out, the tracking sensor wire 255 extends outside of the reusable cable 440 and connects to the interface 410. The tracking sensor wire 255 may be shielded or unshielded within the disposable cable 420 and shielded outside of the disposable cable 420. In another embodiment, the tracking sensor wire 255 may extend inside of the disposable cable 420 and the reusable cable 440, as shown in FIG. 4B. In this embodiment, the tracking sensor wire 255 branches out from the reusable cable 440 just prior to the reusable connector 450 and connect to the interface 410. In still another embodiment, the tracking sensor wire 255 may be integrated into the disposable cable 420 and the reusable cable 440, as shown in FIG. 4C, and is not visible to the clinician. Here, the tracking sensor wire 255 extends from the reusable connector 450 to connect to the tracking system 100.

Figure 5:
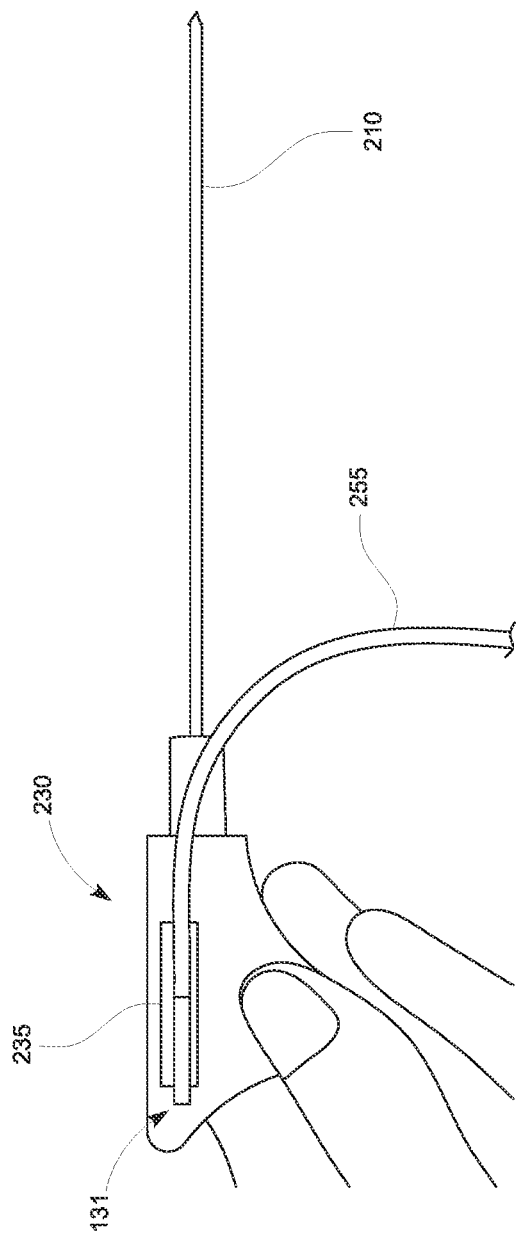
FIG. 5 is a graphical representation illustrating the tracking sensor 131 affixed to the hub 230 of FIG. 2 in accordance with embodiments of the present disclosure.

In another embodiment of the tracking system 100, the tracking sensor 131a or 131b may be positioned on an outer surface of the hub 230 as shown in FIG. 5, in accordance with an embodiment of the present disclosure. This configuration provides clinicians another option to utilize the tracking sensor 131a or 131b in the tracking system 100 in a case that the clinicians already have the treatment probe 130 and do not want to buy additional treatment probes with a tracking sensor integrated thereon. The hub 230 may include a recess 235 or other mechanism designating a predetermined location thereon, within which the tracking sensor 131a or 131b may be fixedly disposed. The recess 235 prevents the tracking sensor 131 from moving with respect to the distal end of the antenna 210. In this way, a spatial relationship between the tracking sensor 131a or 131b and the distal end of the antenna 210 is maintained substantially constant during use of the treatment probe 130. In an embodiment, the handle body 222 encloses the hub 230 to thereby further affix the tracking sensor 131 to the hub body 232. As a result, movement of the tracking sensor 131a or 131b with respect to the distal end of the antenna 210 is further minimized.

Figure 6B:
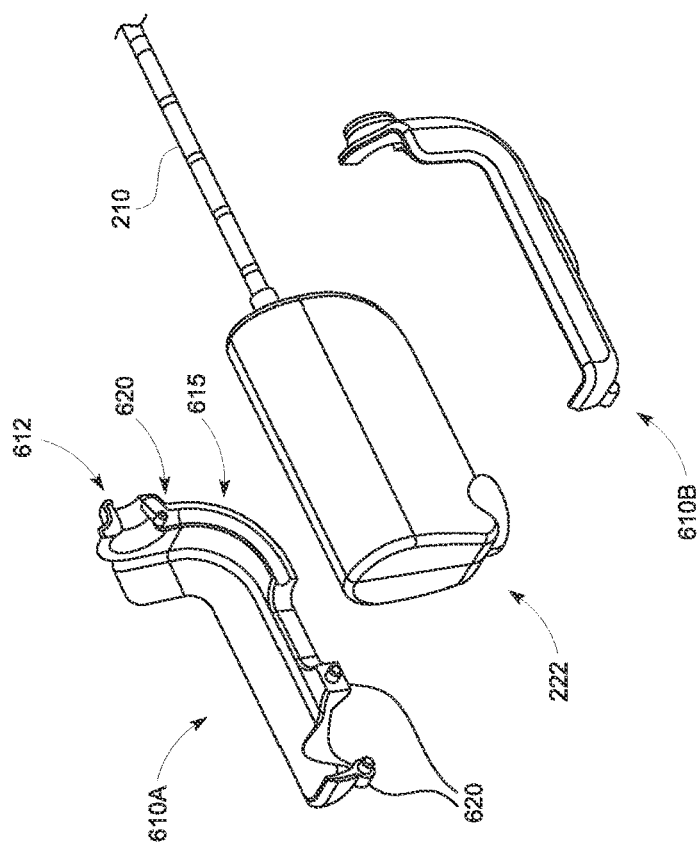
FIGS. 6A and 6B are graphical representations illustrating a pair of retrofits for a sensor wire for the treatment probe 130 in accordance with embodiments of the present disclosure.
Figure 6A:
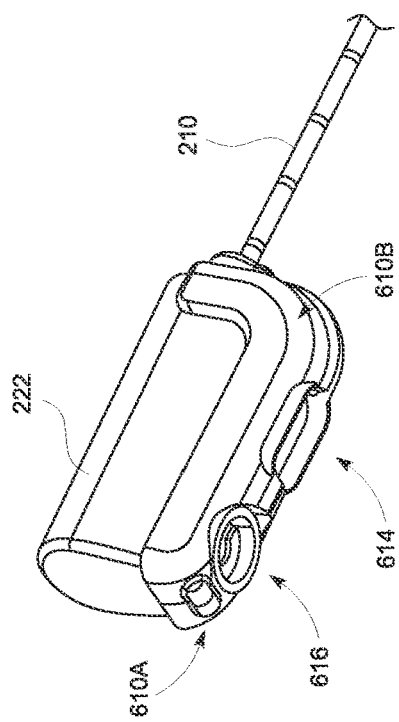

When the tracking sensor 131 is affixed within the recess 235 of the hub 230, a pair of retrofit clips 610a, 610b may provide organization to the cable 250 and tracking sensor wires 255, in an embodiment, as depicted in FIGS. 6A and 6B. FIG. 6A is a perspective view of the retrofit clips 610a and 610b and the handle body 222 in an assembled state, while FIG. 6B is an exploded view of the retrofit clips 610a and 610b in relation to the handle body 222. When assembled, the retrofit clips 610a, 610b include an opening 612 at the front of the handle body 222 through which the antenna 210 extends, an opening 614 for receiving the coolant supply system 240, and an opening 616 for receiving the cable 250. The retrofit clips 610a and 610b form a recess 615 configured to maintain the tracking sensor wire 255 within the retrofit clips 610a, 610b.

To couple the retrofit clips 610a, 610b together, in an aspect, one retrofit clip 610a may include two or more posts 620, and the other retrofit clip 610b may include sockets (not shown) corresponding to the posts 620. The posts 620 and sockets may vary in size and have about 0.004 inch diametral interference. The number and the size of the posts 620 may be adjusted to sufficiently secure the mating between the retrofit clips 610a and 610b. The sockets and the posts 620 are configured to mate with each other to thereby firmly couple the retrofit clips 610a and 610b together and cover the handle body 222. In another aspect, the pair of retrofit clips 610a and 610b may be glued together. In still another aspect, the posts 620 may serve as an anchor for a high tensile strength fiber, which may be wrapped around the posts 620 and glued in place.

Figure 7:
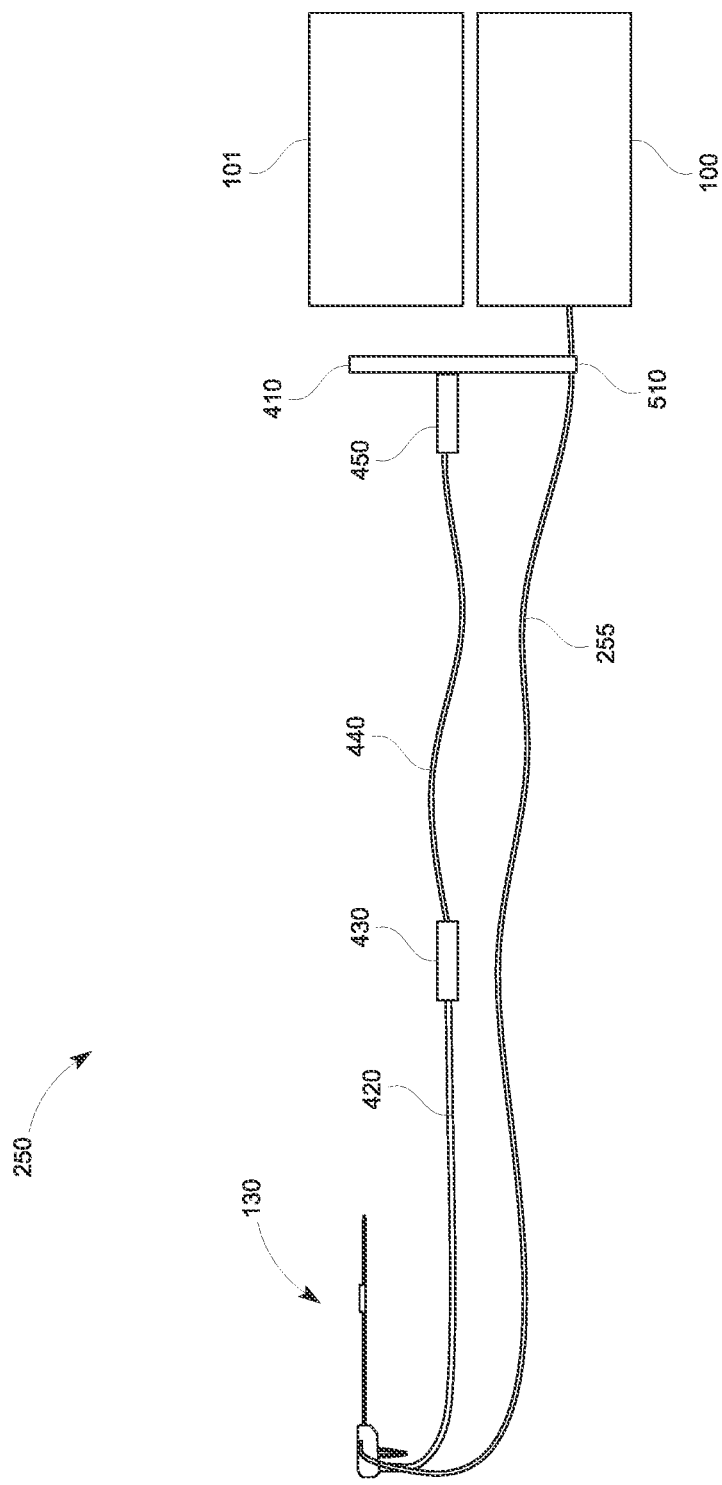
FIG. 7 is a graphical representation illustrating a cable management configuration for the tracking sensor 131 in accordance with embodiments of the present disclosure.

FIG. 7 is a simplified diagram of the tracking system 100 including the tracking sensor 131 affixed on the outer surface of the hub body 232 as shown in FIG. 5 showing a cable management configuration in accordance with an embodiment of the present disclosure. In this embodiment, the tracking sensor wire 255 does not extend within the cable 250 and runs separately from the disposable cable 420 and the reusable cable 440. The tracking sensor wire 255 separately connects to the tracking system 100 via the interface 510. By separating the tracking sensor wire 255 from the cable 250, potential interference between the tracking sensor wire 255 and the temperature sensor wire 256 and/or the transmission line for the antenna 210 may be prevented. In an aspect, the tracking sensor wire 255 may be shielded or unshielded.

Turning now to FIG. 8, a simplified block diagram is provided of a computing device 800, which can be implemented as part of the tracking system 100, the workstation 102, or the ultrasound workstation 150. The computing device 800 may include a memory 802, a processor 804, a display 806, a network interface 808, an input device 810, and/or an output module 812.

The memory 802 includes any non-transitory computer-readable storage media for storing data and/or software that is executable by the processor 804 and which controls the operation of the computing device 800. In an embodiment, the memory 802 may include one or more solid-state storage devices such as flash memory chips. Alternatively or in addition to the one or more solid-state storage devices, the memory 802 may include one or more mass storage devices connected to the processor 804 through a mass storage controller (not shown) and a communications bus (not shown). Although the description of computer-readable media contained herein refers to a solid-state storage, it should be appreciated by those skilled in the art that computer-readable storage media can be any available media that can be accessed by the processor 804. That is, computer readable storage media includes non-transitory, volatile and non-volatile, removable and non-removable media implemented in any method or technology for storage of information such as computer-readable instructions, data structures, program modules or other data. For example, computer-readable storage media includes RAM, ROM, EPROM, EEPROM, flash memory or other solid state memory technology, CD-ROM, DVD, Blu-Ray or other optical storage, magnetic cassettes, magnetic tape, magnetic disk storage or other magnetic storage devices, or any other medium which can be used to store the desired information and which can be accessed by the computing device 800.

The memory 802 may store application 816 and/or CT data 814. The application 816 may, when executed by processor 804, cause the display 806 to present the user interface 818.

The processor 804 may be a general purpose processor, a specialized graphics processing unit (GPU) configured to perform specific graphics processing tasks while freeing up the general purpose processor to perform other tasks, and/or any number or combination of such processors.

The display 806 may be touch-sensitive and/or voice-activated, enabling the display 806 to serve as both an input and output device. Alternatively, a keyboard (not shown), mouse (not shown), or other data input devices may be employed.

The network interface 808 may be configured to connect to a network such as a local area network (LAN) consisting of a wired network and/or a wireless network, a wide area network (WAN), a wireless mobile network, a Bluetooth network, and/or the internet. For example, the computing device 800 may receive, through the network interface 808, computed tomographic (CT) image data of a patient from a server, for example, a hospital server, internet server, or other similar servers, for use during surgical ablation planning. Patient CT image data may also be provided to the computing device 800 via a removable memory. The computing device 800 may receive updates to its software, for example, the application 816, via the network interface 808. The computing device 800 may also display notifications on the display 806 that a software update is available.

The input device 810 may be any device by means of which a user may interact with the computing device 800, such as, for example, a mouse, keyboard, foot pedal, touch screen, and/or voice interface.

The output module 812 may include any connectivity port or bus, such as, for example, parallel ports, serial ports, universal serial busses (USB), or any other similar connectivity port known to those skilled in the art.

The application 816 may be one or more software programs stored in memory 802 and executed by processor 804 of the computing device 800. During a planning phase, the application 816 guides a clinician through a series of steps to identify a target, size the target, size a treatment zone, and/or determine an access route to the target for later use during the procedure phase. In some embodiments, application 816 is loaded on computing devices in an operating room or other facility where surgical procedures are performed, and is used as a plan or map to guide a clinician performing a surgical procedure.

The application 816 may be installed directly on the computing device 800, or may be installed on another computer, for example a central server, and opened on the computing device 800 via network interface 808. The application 816 may run natively on the computing device 800, as a web-based application, or any other format known to those skilled in the art. In some embodiments, the application 816 will be a single software program having all of the features and functionality described in the present disclosure. In other embodiments, the application 816 may be two or more distinct software programs providing various parts of these features and functionality. For example, the application 816 may include one software program for use during the planning phase, and a second software program for use during the treatment phase. In such instances, the various software programs forming part of the application 816 may be enabled to communicate with each other and/or import and export various settings and parameters relating to the navigation and treatment and/or the patient to share information. For example, a treatment plan and any of its components generated by one software program during the planning phase may be stored and exported to be used by a second software program during the procedure phase.

The application 816 communicates with a user interface 818 which generates a user interface for presenting visual interactive features to a clinician, for example, on the display 806 and for receiving clinician input, for example, via a user input device. For example, the user interface 818 may generate a graphical user interface (GUI) and output the GUI to the display 806 for viewing by a clinician.

The computing device 800 may be linked to the display 110, thus enabling the computing device 800 to control the output on the display 110 along with the output on the display 806. The computing device 800 may control the display 110 to display output which is the same as or similar to the output displayed on the display 806. For example, the output on the display 806 may be mirrored on the display 110. Alternatively, the computing device 800 may control the display 110 to display different output from that displayed on the display 806. For example, the display 110 may be controlled to display guidance images and information during the surgical procedure, while the display 806 is controlled to display other output, such as configuration or status information of an electrosurgical generator 101 as shown in FIG. 1.

Although embodiments have been described in detail with reference to the accompanying drawings for the purpose of illustration and description, it is to be understood that the inventive processes and apparatus are not to be construed as limited thereby. It will be apparent to those of ordinary skill in the art that various modifications to the foregoing embodiments may be made without departing from the scope of the disclosure.

What is claimed is:

1. A surgical system, comprising:
   a treatment probe having a handle assembly and an antenna, the antenna having a distal end portion disposed outside of the handle assembly and a proximal end portion disposed within the handle assembly, the treatment probe configured to operably couple to an electrosurgical generator for delivering electrosurgical energy to tissue via the antenna, the antenna including an outer conductor and a balun surrounding the outer conductor;
   an inflow tube coaxially surrounding the outer conductor to define a first lumen configured to receive a fluid for cooling the antenna;
   a cooling jacket coaxially surrounding the inflow tube to define a second lumen configured to receive the fluid;
   a first cable extending from the handle assembly and having a distal end disposed within the handle assembly and a proximal free end opposite the distal end connected to a connector assembly such that the connection between the proximal free end and the connector assembly is disposed outside of the handle assembly and the connector assembly is configured to be out of physical contact with the treatment probe during use of the treatment probe to deliver the electrosurgical energy to the tissue via the antenna;
   a second cable having a distal end configured to releasably connect to the connector assembly and a proximal end opposite the distal end configured to be coupled to the electrosurgical generator;
   a tracking sensor disposed on an outer surface of the cooling jacket and configured to communicate with a tracking system via a tracking sensor wire, the tracking sensor wire configured to transmit a location signal from the tracking sensor to the tracking system for determining a location of the treatment probe, the tracking sensor wire extending through the handle assembly and through at least one of the first cable or the second cable to electrically couple to the tracking system; and
   a temperature sensor disposed within the antenna, the temperature sensor connected to the connector assembly by a temperature sensor wire extending through the antenna, the handle assembly, the first cable, and into the connector assembly, the temperature sensor wire configured to transmit a sensed temperature signal from the temperature sensor to the connector assembly, wherein the tracking system determines the location of the treatment probe based at least in part on the sensed temperature signal and a material forming the tracking sensor wire.

2. The surgical system according to claim 1, wherein the tracking sensor wire extends through the handle assembly and through a portion of the first cable, and branches out from the first cable at a location distal to the connector assembly such that the tracking sensor wire is not disposed within the connector assembly or the second cable.

3. The surgical system according to claim 1, wherein the tracking sensor wire extends through the handle assembly, the first cable, the connector assembly, and the second cable.

4. The surgical system according to claim 1, further comprising an interface configured to connect to the proximal end of the second cable to electrically couple the second cable to the electrosurgical generator and the tracking system.

5. The surgical system according to claim 1, wherein the connector assembly is configured to communicate the sensed temperature signal to the tracking system via the second cable.

6. The surgical system according to claim 1, wherein the temperature sensor is disposed within the first lumen defined by the inflow tube.

7. The surgical system according to claim 1, wherein the antenna includes a coaxial cable electrically coupled to the first cable, at least a portion of the coaxial cable disposed within the first lumen defined by the inflow tube.

8. The surgical system according to claim 1, further comprising a memory disposed within the connector assembly and storing a spatial relationship between the tracking sensor and a distal end of the treatment probe.

9. A surgical system, comprising:
   an electrosurgical generator;
   a tracking system;
   a treatment probe having a handle assembly and an antenna, the antenna having a distal end portion disposed outside of the handle assembly and a proximal end portion disposed within the handle assembly, the treatment probe configured to operably couple to the electrosurgical generator for delivering electrosurgical energy to tissue via the antenna, the antenna including an outer conductor and a balun surrounding the outer conductor;
   an inflow tube coaxially surrounding the outer conductor to define a first lumen configured to receive a fluid for cooling the antenna;
   a cooling jacket coaxially surrounding the inflow tube to define a second lumen configured to receive the fluid;
   a disposable cable extending from the handle assembly and having a distal end disposed within the treatment probe and a proximal free end opposite the distal end connected to a connector assembly such that the connection between the proximal free end and the connector assembly is disposed outside of the handle assembly and the connector assembly is configured to be out of physical contact with the treatment probe during use of the treatment probe to deliver the electrosurgical energy to the tissue via the antenna;
   a reusable cable having a distal end configured to releasably connect to the connector assembly and a proximal end opposite the distal end configured to be coupled to the electrosurgical generator and the tracking system;

a tracking sensor disposed on an outer surface of the cooling jacket and configured to communicate with the tracking system;

a tracking sensor wire interconnecting the tracking sensor and the tracking system, the tracking sensor wire configured to transmit a location signal from the tracking sensor to the tracking system for determining a location of the treatment probe, the tracking sensor wire extending through the handle assembly and through at least one of the disposable cable or the reusable cable to electrically couple to the tracking system;

a temperature sensor disposed on the outer conductor and out of physical contact with the balun; and a temperature sensor wire interconnecting the temperature sensor and the connector assembly, the temperature sensor wire extending through the antenna, the handle assembly, the disposable cable, and into the connector assembly and configured to transmit a sensed temperature signal from the temperature sensor to the connector assembly, wherein the tracking system determines the location of the treatment probe based at least in part on the sensed temperature signal and a material forming the tracking sensor wire.

10. The surgical system according to claim 9, wherein the tracking sensor wire extends through the handle assembly and through a portion of the disposable cable, and branches out from the disposable cable at a location distal to the connector assembly such that the tracking sensor wire is not disposed within the connector assembly or the reusable cable.

11. The surgical system according to claim 9, wherein the tracking sensor wire extends through the handle assembly, the disposable cable, the connector assembly, and the reusable cable.

12. The surgical system according to claim 9, wherein the temperature sensor is disposed within the first lumen defined by the inflow tube.

13. The surgical system according to claim 9, wherein the antenna includes a coaxial cable electrically coupled to the disposable cable, at least a portion of the coaxial cable disposed within the first lumen defined by the inflow tube.

14. A treatment probe, comprising:

a handle assembly;

an antenna extending from the handle assembly and configured to operably couple to an electrosurgical generator for delivering electrosurgical energy to tissue, the antenna having a distal end portion disposed outside of the handle assembly and a proximal end portion disposed within the handle assembly, the antenna including an outer conductor and a balun surrounding the outer conductor;

an inflow tube coaxially surrounding the outer conductor to define a first lumen configured to receive a fluid for cooling the antenna;

a cooling jacket coaxially surrounding the inflow tube to define a second lumen configured to receive the fluid;

a disposable cable extending from the handle assembly and having a distal end disposed within the treatment probe and a proximal free end opposite the distal end connected to a connector assembly such that the connection between the proximal free end and the connector assembly is disposed outside of the handle assembly and the connector assembly is configured to be out of physical contact with the handle assembly during use of the antenna to deliver the electrosurgical energy to the tissue, the connector assembly configured to releasably connect to a reusable cable connected to the electrosurgical generator to electrically couple the treatment probe to the electrosurgical generator;

a tracking sensor disposed on an outer surface of the cooling jacket and configured to communicate with a tracking system via a tracking sensor wire, the tracking sensor wire configured to transmit a location signal from the tracking sensor to the tracking system for determining a location of the treatment probe, the tracking sensor wire extending through the handle assembly and through at least a portion of the disposable cable; and a temperature sensor disposed on the outer conductor and out of physical contact with the balun, the temperature sensor connected to the connector assembly by a temperature sensor wire extending through the antenna, the handle assembly, the disposable cable, and into the connector assembly, the temperature sensor wire configured to transmit a sensed temperature signal from the temperature sensor to the connector assembly, wherein the tracking system determines the location of the treatment probe based at least in part on the sensed temperature signal and a material forming the tracking sensor wire.

15. The treatment probe according to claim 14, wherein the tracking sensor wire extends through the handle assembly and through a portion of the disposable cable, and branches out from the disposable cable at a location distal to the connector assembly.

* * * * *